US00PP23132P2

(12) United States Plant Patent
MacGregor et al.

(10) Patent No.: US PP23,132 P2
(45) Date of Patent: Oct. 23, 2012

(54) ***ANEMONE* PLANT NAMED 'MACANE001'**

(50) Latin Name: ***Anemone* hybrid**
Varietal Denomination: MACANE001

(76) Inventors: Elizabeth MacGregor, Kirkcudbright (GB); Alasdair John MacGregor, Kirkcudbright (GB)

( * ) Notice: Subject to any disclaimer, the term of this patent is extended or adjusted under 35 U.S.C. 154(b) by 0 days.

(21) Appl. No.: 13/135,169

(22) Filed: Jun. 27, 2011

(51) Int. Cl.
*A01H 5/00* (2006.01)

(52) U.S. Cl. ..... Plt./263.1
(58) Field of Classification Search ..... Plt./263.1
See application file for complete search history.

*Primary Examiner* — June Hwu
*Assistant Examiner* — Louanne Krawczewicz Myers
(74) *Attorney, Agent, or Firm* — Cassandra Bright

(57) ABSTRACT

A distinct new cultivar of *Anemone* plant named 'MACANE001', characterized by an exceptionally long flowering season, upright, vigorous, free flowering and perennial plant habit with large white flowers having bluish violet banding on the reverse of the sepals. The new cultivar is an *Anemone* typically suited for ornamental container and landscape use.

2 Drawing Sheets

Figure 1:
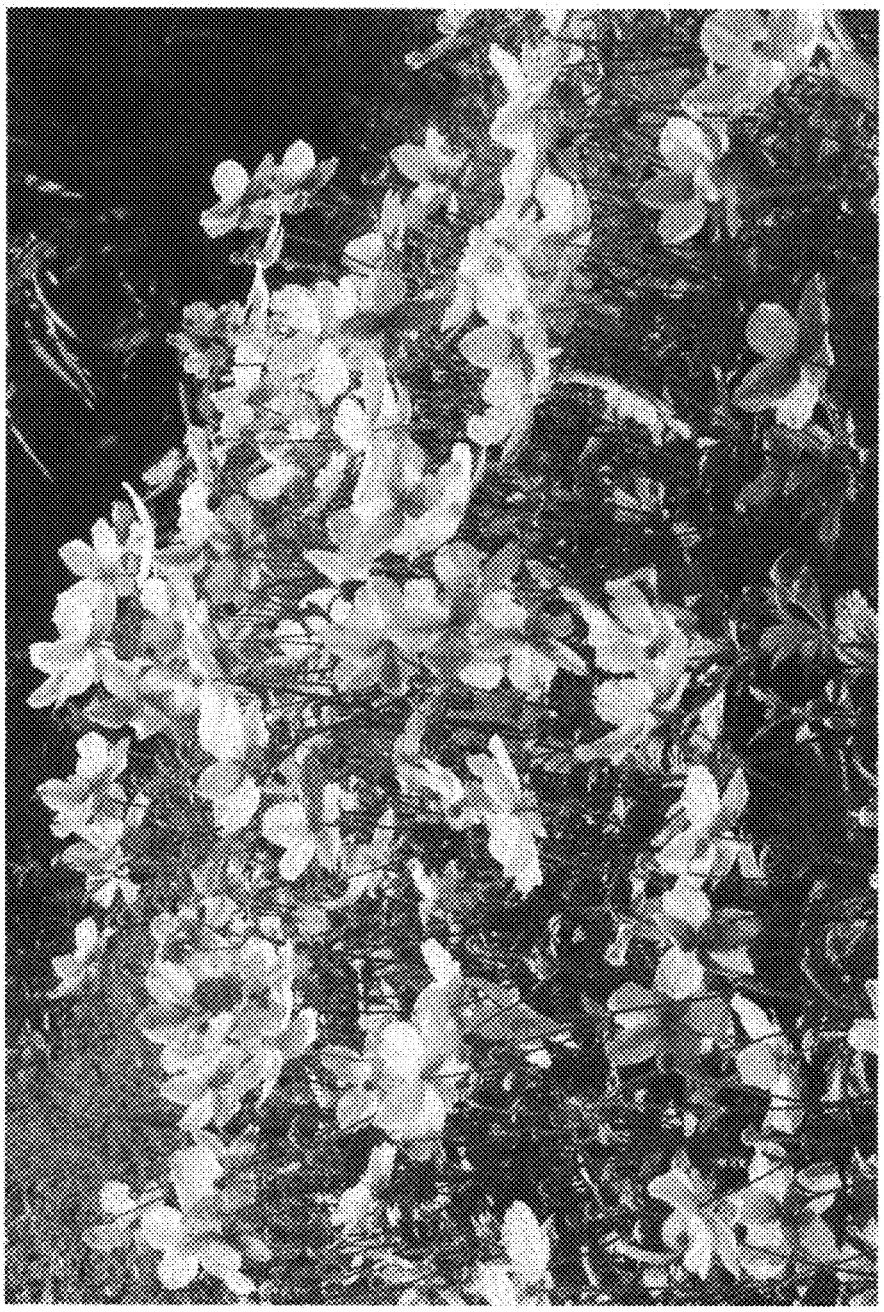

Latin name of the genus and species: *Anemone* hybrid.
Variety denomination: 'MACANE001'.

BACKGROUND OF THE INVENTION

The new *Anemone* was discovered by the inventors, Elizabeth and Alasdair MacGregor, as a chance seedling in a group of *Anemone rupicola* seedlings, growing in a protected poly tunnel greenhouse at a commercial nursery, in Kirkcudbright, Scotland, in 2001.

The seed had been collected from *Anemone rupicola* plants grown in a walled garden, in an area also containing *Anemone hybrida* and *Anemone hupehensis* cultivars (not patented). The very vigorous habit and exceptionally long flowering season of *Anemone* 'MACANE001' indicates that one of the aforementioned cultivars was the pollen parent, however the inventors are unable to confirm this.

Asexual reproduction by root cuttings has been undertaken in 2003, by the inventors in their own nursery in Kirkcudbright, Scotland. Plants produced have proved to be stable and reproduced true to type in successive generations. After several years experimentation in a commercial research laboratory in the Netherlands, tissue culture plants have also been produced and have also proved to be stable and true to type. Commercial production was not undertaken until tissue culture plantlets could be supplied to the market in Fall 2010.

SUMMARY OF THE INVENTION

The cultivar 'MACANE001' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'MACANE001'. These characteristics in combination distinguish 'MACANE001' as a new and distinct *Anemone* cultivar:

1. Exceptionally long flowering season, typically in Scotland from the end of April until November in protected conditions and from early June until November outdoors.
2. Large white flowers with distinctive bluish-violet banding on the reverse of the sepals.
3. Vigorous, perennial garden performance

PARENTAL COMPARISON

Plants of the new cultivar 'MACANE001' are similar to the seed parent, *Anemone rupicola* in most horticultural characteristics. However, plants of 'MACANE001' differ in that they are larger and more vigorous, and more floriferous. Additionally, the new variety produces larger flowers, with more distinct coloration on the petal reverse. The flowering season for 'MACANE001' is longer, and flowering more consistent during the season than for *Anemone rupicola.*

COMMERCIAL COMPARISON

Plants of the new cultivar 'MACANE001' are similar to the known commercial variety, *Anemone hybrida* 'Honorine Jobert' in some horticultural characteristics. However, plants of 'MACANE001' differ in that they are shorter, and more floriferous. Additionally, the new variety produces flowers with more distinct coloration on the petal reverse. The flowering season for 'MACANE001' begins at least 2 months earlier than 'Honorine Jobert'.

Plants of the new cultivar 'MACANE001' are similar to the known commercial variety, *Anemone multifida* 'Annabella White' in some horticultural characteristics. However, plants of 'MACANE001' differ in that they are taller, more vigorous, and more floriferous. Additionally, the new variety produces larger flowers, with more distinct coloration on the petal reverse. The flowering season for 'MACANE001' begins at least 1 month earlier than 'Annabelle White'.

BRIEF DESCRIPTION OF THE PHOTOGRAPH

The accompanying photograph in FIG. 1 illustrates in full color a typical plants of 'MACANE001' grown outdoors in a garden in Kirkcudbright, Scotland. This plant is approximately 15 months old.

Figure 2:
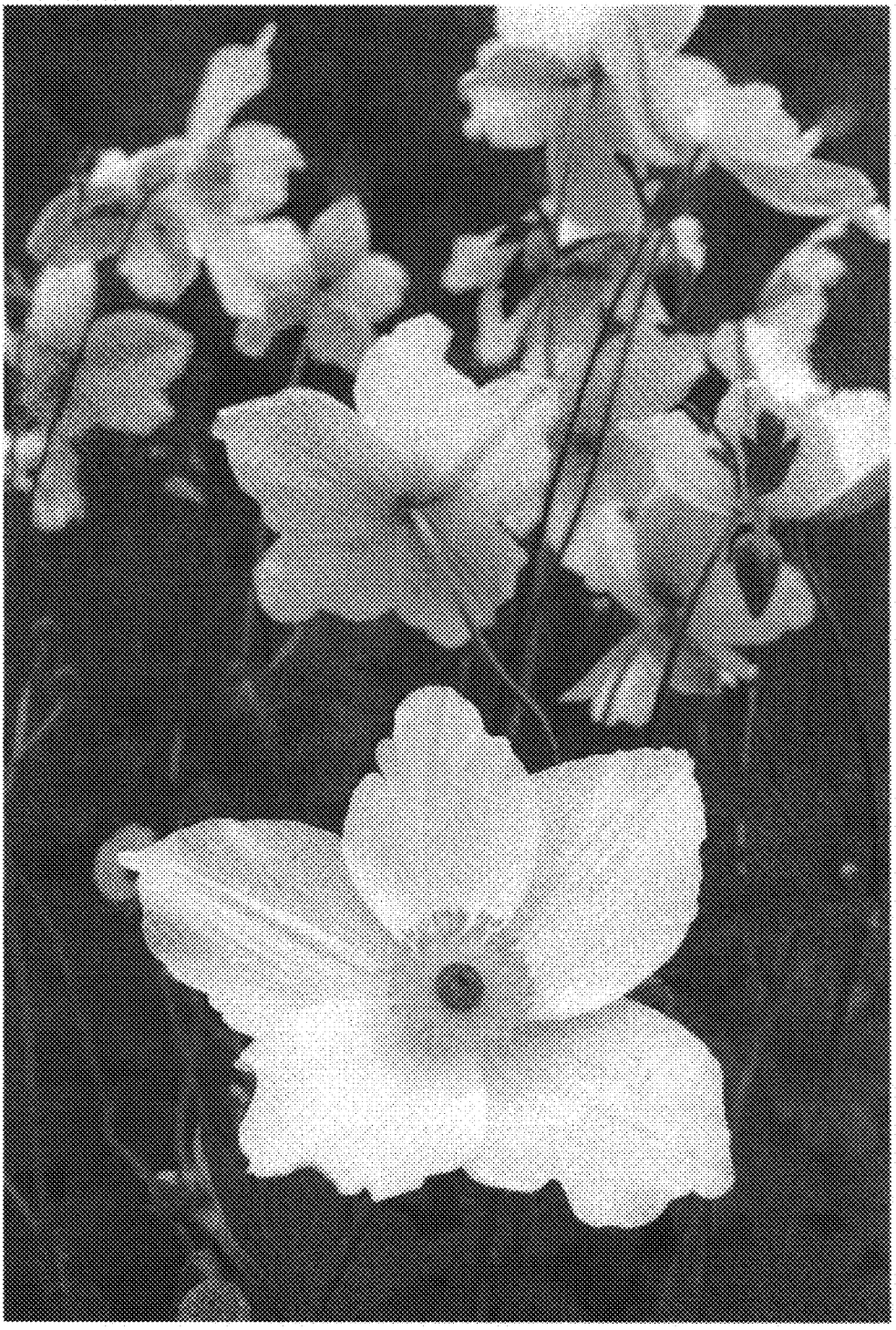

FIG. 2 illustrates a close up of the flower, front and reverse. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2001, except where general terms of ordinary dictionary significance are used. The following observations and measurements describe 'MACANE001' plants grown outdoors in Kirkcudbright, Scotland at a commercial nursery. The growing temperature ranged from 0° C. to 12° C. at night to 8° C. to 22° C. during the day. During the winter period December to March, plants were sheltered in a large poly-tunnel with day temperatures ranging from 5° C. to 18° C., and night temperatures ranging from −5° C. to +8° C. No artificial light, photoperiodic treatments or chemical treatments were given to the plants. Measurements and numerical values represent averages of typical flowering types.

Botanical classification: *Anemone* hybrid 'MACANE001'.

Age of the plant described: Approximately 15 months.

Container size of the plant described: 3 liter commercial container.

PROPAGATION

Time to produce a flowering plant from root-cutting: Nine to twelve months.

Root description: Fibrous, reddish-brown (not RHS identified) in color.

Rooting habit: Dense, freely branching.

PLANT

Plant and growth habit: Vigorous, upright, mounding perennial; leaves and inflorescences densely tufted, arising at or just below ground level from a subterranean, vertical, woody main stem about 10 cm long.

Plant height: 40 to 60 cm.

Plant diameter: 30 to 40 cm.

FOLIAGE

Arrangement: Alternate, simple.

Length of blade: 5 to 6 cm.

Width of blade: 8 to 9 cm.

Shape of blade: Broadly ovate, palmately 3-lobed to about 5 mm from base; lobes oblong-cuneate, unevenly 2 or 3-lobed. Lobes average length 4.5 to 5 cm. Average lobe width approximately 2 cm.

Apex: Acute.

Base: Widely cordate.

Margin: Sharply serrate to biserrate in upper half.

Texture, upper surface: Glabrous, matte.

Texture, lower surface: Weakly pilose, especially near veins.

Venation pattern: Palmate.

*Color*.—Developing foliage, upper surface: Close to Green 141B. Developing foliage, lower surface: Close to Green 138B. Fully expanded foliage, upper surface: Green 143A to Green 143B; Venation, Yellow-Green 144B. Fully expanded foliage, lower surface: Close to Green 138B; Venation, Green 138B.

*Petiole*.—Length: To about 25 cm. Diameter: About 1.5 mm. Cross-section: Cylindrical, grooved adaxially. Texture, upper and lower surfaces: Glabrous to very sparsely pilose. Color, upper and lower surfaces: Close to Yellow-Green 145A.

FLOWER

*Flower arrangement and habit*.—Single, saucer-shaped flowers arranged in dichasial cymes with long peduncles and pedicels, 2 or 3 per cyme, occasionally solitary. Two or three bracts (similar to small leaf-lobes) are borne at the top of each peduncle, with a smaller pair 2 to 4 cm below the second and third flowers in each cyme. Flowers nodding in bud, upright when open. Mature flowers close and nod from evening to morning. Flowers not fragrant.

*Natural flowering season*.—From June to November outdoors in south-west Scotland. Individual flowers last about 8 to 14 days before the sepals fall.

*Inflorescence height*.—25 to 60 cm.

*Inflorescence diameter*.—About 15 cm.

*Flower diameter*.—About 9 cm.

*Flower length* (*depth*).—About 2.5 cm.

*Flower bud*.—Shape: Ovoid. Length: 1.5 to 2 cm. Diameter: 8 to 10 mm. Color: Close to 86A. Texture: Densely pubescent.

*Petals*.—Absent.

*Sepals*.—Quantity/arrangement: Five arranged in a single whorl, radially symmetrical. Length: 4 to 4.5 cm. Width: 2.5 to 3 cm. Shape: Obovate to elliptical. Apex: Broadly obtuse to rounded, sometimes erose or notched. Base: Cuneate. Margin: Entire, sometimes sinuous or shallowly lobed near apex. Texture: upper surface: Glabrous, silky matte. Texture: lower surface: Finely pubescent. Color: When opening, upper surface (all sepals): Close to White 155C, though whiter. When opening, lower surface (outer, bud-enclosing sepals): Violet-Blue 89A near base, shading outwards to Violet 87B or Violet 88C, sometimes partly white (close to 155C). When opening, lower surface (intermediate sepal): As outer sepal but ½ to ¾ white (close to 155C). When opening, lower surface (inner sepals): Close to 155C, streaked centrally and near base with Violet 87D. Fully opened, upper surface: Close to 155C, though whiter. Fully opened, lower surface (outer, bud-enclosing sepals): Violet-Blue 91C streaked with Violet 88A, sometimes partly white (close to 155C). Fully opened, lower surface (intermediate sepal): As outer sepal but ½ to ¾ white (close to 155C). Fully opened, lower surface (inner sepals): Close to 155C, faintly streaked centrally and near base with Violet 88D. Peduncles: Length: 20 to 30 cm. Diameter: 1.5 to 2 mm. Aspect: Erect or slightly leaning. Texture: Appressed pubescent, more densely above. Color: Near Yellow-Green 146B to C, tinged with Violet 87B to C where exposed. Pedicels: Length: 8 to 20 cm. Diameter: 1 to 1.5 mm. Aspect: Upright to about 30 degrees from vertical. Texture: Appressed pubescent, more densely above. Color: Near Yellow-Green 146B to C, tinged with Violet 87B to C below and where exposed. Bracts: Length: Approximately 1.5 to 3.0 cm. Width: Approximately 1.0 to 2.0 cm. Shape: Obovate to orbicular. Apex: Broadly obtuse to rounded. Base: Cuneate. Margin:

Entire. Texture: upper surface: Glabrous. Texture: lower surface: Finely pubescent. Color: Upper surface: Near RHS Yellow-Green 144B. Lower surface: Near RHS Green 138B.

REPRODUCTIVE ORGANS

*Androecium*.—Stamen number per flower: About 200. Filament length: 6 to 9 mm. Filament diameter: About 0.3 mm. Filament color: Close to Yellow 7D. Anther shape: Narrowly ellipsoid. Anther length: 1.0 to 1.5 mm. Anther color: Near Yellow-Orange 20A. Amount of pollen: Scarce, mostly colorless, appears empty and sterile.

*Gynoecium*.—Pistil number per flower: About 200. Pistil length: About 2 mm. Stigma diameter: About 0.4 mm. Stigma shape: Reflexed spathulate. Stigma color: Greyed-Purple 185A. Style length: 0.2 to 0.3 mm. Style color: Close to Yellow-Green 144B. Ovary color: Close to Yellow-Green 144B.

OTHER CHARACTERISTICS

Seed/fruit: Very few fertile seeds have been found, the plant is effectively sterile.

Garden performance: Plants of the new *Anemone* have good garden performance and are hardy. USDA Hardiness tested in Scotland to zone 7, untested but expected to be suitable for zone 6.

Diseases and pests: Neither resistance nor susceptibility to normal diseases and pests of *Anemone* has been observed.

What is claimed is:

1. A new and distinct cultivar of *Anemone* hybrid plant named 'MACANE001' as herein illustrated and described.

* * * * *